United States Patent

Sugimoto et al.

[11] Patent Number: 5,146,779
[45] Date of Patent: Sep. 15, 1992

[54] INDENTATION HARDNESS TESTER

[75] Inventors: Takao Sugimoto, Sagamihara; Takehiro Nishimura, Muroran; Yohichi Fujikake; Akiomi Yamaguchi, both of Kimitsu, all of Japan

[73] Assignee: Nippon Steel Corporation, Tokyo, Japan

[21] Appl. No.: 807,734

[22] Filed: Dec. 16, 1991

Related U.S. Application Data

[63] Continuation of Ser. No. 576,968, Sep. 4, 1990, abandoned.

[30] Foreign Application Priority Data

Sep. 5, 1989 [JP] Japan .................................. 1-230053

[51] Int. Cl.$^5$ .............................................. G01N 3/48
[52] U.S. Cl. ........................................ 73/81; 356/378
[58] Field of Search ..................... 73/81-83; 358/107

[56] References Cited

U.S. PATENT DOCUMENTS

| | | |
|---|---|---|
| 4,182,164 | 1/1980 | Fohey . |
| 4,255,966 | 3/1981 | Batie . |
| 4,312,220 | 1/1982 | Borgersen . |
| 4,354,761 | 10/1982 | Jacoby .................. 356/378 |
| 4,463,600 | 8/1984 | Hobbs et al. . |
| 4,653,106 | 3/1987 | Yamatsuta et al. ............. 73/81 |

FOREIGN PATENT DOCUMENTS 0021136 2/1983 Japan ..................................... 73/81

Primary Examiner—Robert Raevis
Attorney, Agent, or Firm—Cushman, Darby & Cushman

[57] ABSTRACT

An indentation hardness tester determines positions of edge points of an indentation and calculates a hardness number from the length of diagonals of the indentation measured from the position of apexes of the indentation. The positions of apexes of the indentation are detected, for example, from intersection points of lines which approximate sides of the indentation. The indentation hardness tester may comprise a bright field/dark field switching part to obtain a clear image of the indentation.

10 Claims, 20 Drawing Sheets

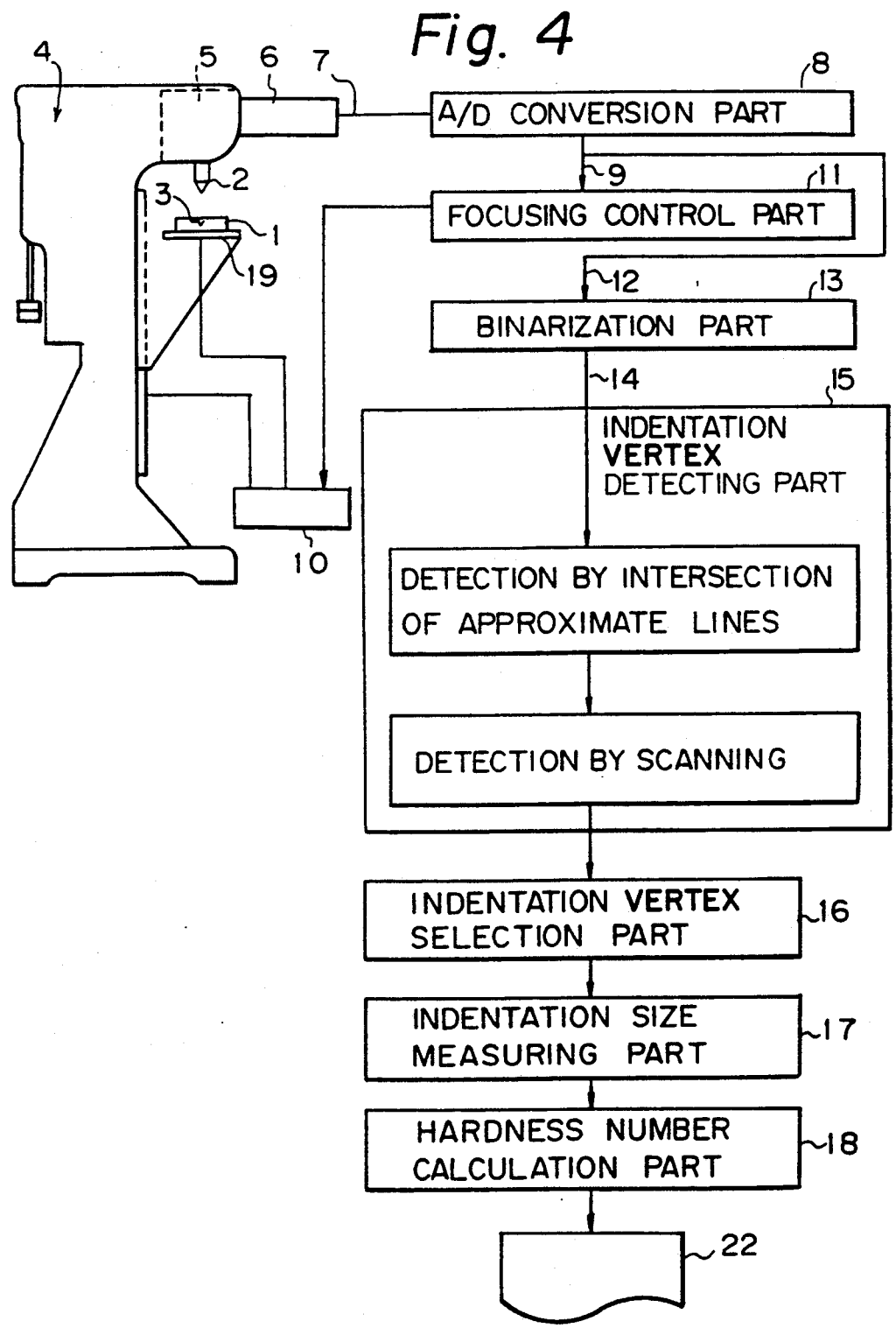

INDENTATION HARDNESS TESTER

This is a continuation of application Ser. No. 07/576,968, filed on Sep. 4, 1990, which was abandoned upon the filing hereof.

BACKGROUND OF THE INVENTION

1. Field of the Invention

The present invention relates to an indentation hardness tester for automatically measuring indentation hardness such as Vickers hardness, Brinell hardness, and the like.

2. Description of the Related Art

Vickers hardness or Brinell hardness is measured to evaluate mechanical characteristics of metal material. A Vickers hardness number is measured by indenting the surface of a test piece with an indenter of a diamond-pyramid shape having face angles of 136 degrees, and by dividing a value of an indenting load by a surface area of a pyramid indentation formed by the indenter. A Brinell number is also measured by dividing a value of an indentation load by a surface area of a spherical indentation formed by an indenter of a steel sphere shape.

A conventional indentation hardness tester is disclosed, for example, in Japanese Examined Patent Publication (Kokoku) No. 63-10379. The indentation hardness tester disclosed in this publication can automatically measure the hardness number, and comprises a testing machine for indenting a surface of a test piece with an indenter under a predetermined load to form indentations, a camera connected to a microscope provided in the testing machine, an A/D conversion part for converting image information obtained in the camera to digital signals in the form of brightness level of, for example, 256 levels, an image processing part for extracting points where the digital image signal from the A/D conversion part abruptly changes, as vertices of the indentation, an indentation size measuring part for calculating the size of the indentation from position data of the vertices of the indentation obtained in the image processing part, and a hardness number calculation part for calculating a hardness number from the size of the indentation calculated in the indentation size measuring part and an indentation load, to output the hardness number to a printer, etc.

The vertices are found by scanning the digital image signal on a measuring axis, in the image processing part. Therefore, if a diagonal line of the indentation does not align with the measuring axis, the indentation size measuring part outputs a wrong value. This situation occurs due to inclination of the indentation caused by microscopic movement in the case where an indented test piece is moved before measurement.

Additionally, if obtained images of the indentation are not clear because of lack of uniformity in brightness of background due to grain boundary, flaw, rust, and the like, the indentation size measuring part likewise outputs a wrong value.

These errors in measurement of hardness number cause a serious problem because the quality characteristics of products can be mistaken.

SUMMARY OF THE INVENTION

It is an object of the present invention to provide an indentation hardness tester wherein the aforementioned shortcoming is overcome.

In accordance with the present invention, there is provided an indentation hardness tester comprising a testing machine for forming an indentation on a testing piece by indenting a surface of the testing piece with a pyramid shape indenter under a predetermined load, a camera attached to a microscope for picking up an image of the indentation, an A/D conversion means for converting image information obtained in the camera to a digital image signal, a binarization means for binarizing the digital image signal to obtain a binary image of the indentation, an indentation vertex determining means for determining positions of vertices of the indentation, an indentation size measuring means for measuring the length of diagonals of the indentation from the positions of vertex determined by the indentation edge point determining means, and a hardness number calculation means for calculating a hardness number from the length of diagonals of indentation measured by the indentation size measuring means and a value of the indenting load.

BRIEF DESCRIPTION OF THE DRAWINGS

FIG. 4 is a diagram representing a first embodiment of an indentation hardness tester according to the present invention;

DESCRIPTION OF THE PREFERRED EMBODIMENTS

Before describing the preferred embodiments according to the invention, examples of aforementioned related art are given with reference to the accompanying drawings.

Figure 1:
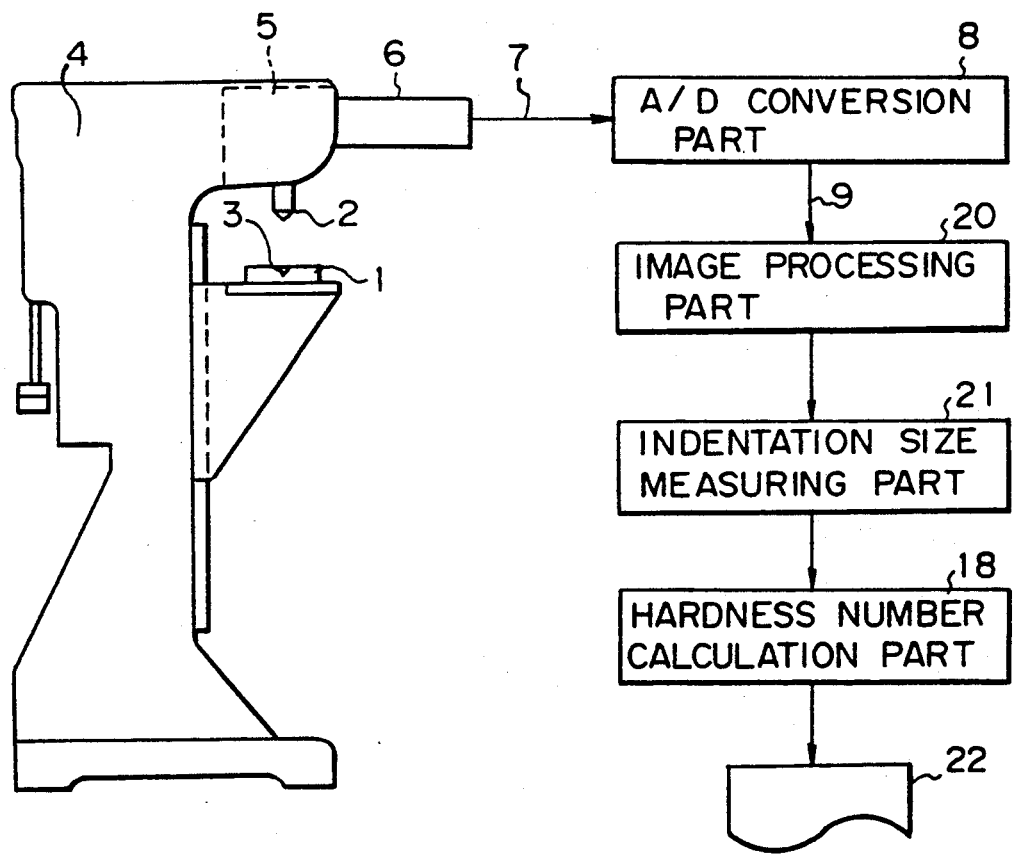
FIG. 1 is a diagram representing an indentation hardness tester of the prior art.

FIG. 1 shows an indentation hardness tester for automatically measuring indentation hardness as disclosed in Japanese Examined Patent Publication (Kokoku) No. 63-10379.

A testing machine 4 comprises an indenter 2 for indenting a surface of a testing piece 1 to form a indentation 3, a microscope 5, and a camera 6 attached to the microscope 5. An A/D conversion part 8 converts image information 7 obtained in the camera 6 to digital signals in the form of brightness levels of, for example, 256 levels. An image processing part 20 finds points where the digital image signal 9 from the A/D conversion part 8 abruptly changes, at vertices of the indentation. An indentation size measuring part 21 calculates size of the indentation from position data of the vertices of the indentation obtained in the image processing part 20. A hardness number calculation part 18 calculates a hardness number from the size of the indentation calculated in the indentation size measuring part 21 and an indentation load, to output the hardness number to a printer 22.

Figure 2A:
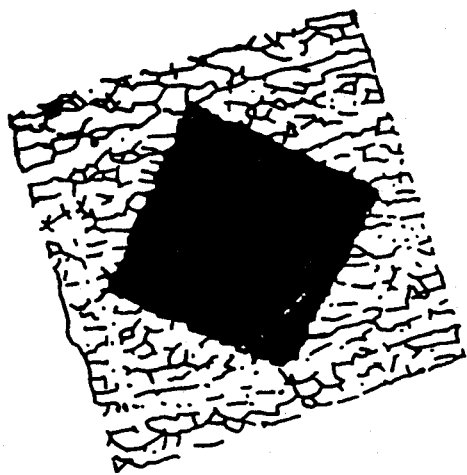
FIGS. 2A and 2B are diagrams showing an example of an inclined image of an indentation.
Figure 2B:
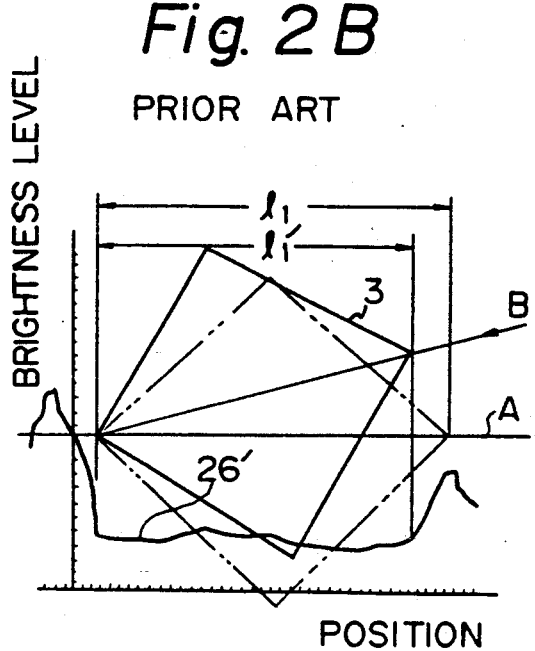

As mentioned before, in the case where an indented test piece is moved before measurement, inclination of the indentation occurs due to microscopic movement, as shown in FIG. 2A. Then, as shown in FIG. 2B, a diagonal line B of the indentation 3 does not align with a measuring axis A, so that the indentation size measuring part 21 outputs a wrong value $l_1'$ though a true value is $l_1$.

Figure 3A:
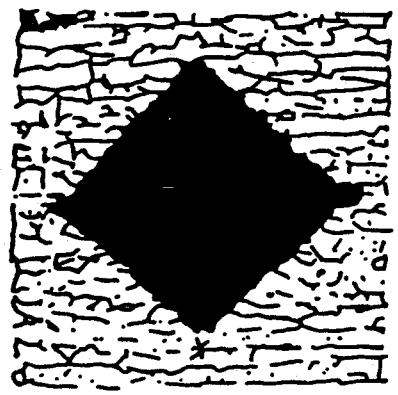
FIGS. 3A and 3B are diagrams showing an example of an image of an indentation having an unclear apex.
Figure 3B:
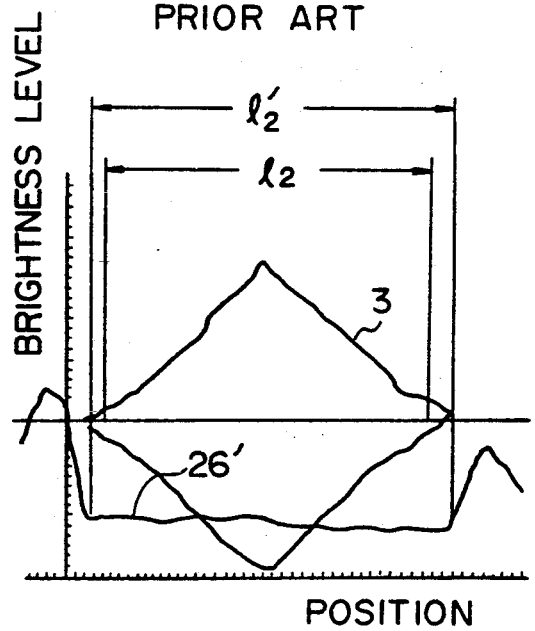

Also, as shown in FIG. 3A, if images of corners of the indentation are not clear because of lack of uniformity in brightness of background due to grain boundary, flaw, rust, and the like, then, as shown in FIG. 3B, the indentation size measuring part likewise outputs a wrong value $l_2'$ though a true value is $l_2$.

The preferred embodiments of the present invention will now be described with reference to the accompanying drawings.

FIG. 4 shows a first embodiment of the present invention. The same reference numerals as used in FIG. 1 are used for constituents which are similar to those in FIG. 1, and thus descriptions thereof are left out. A focusing control part 11 controls an autofocusing part 10 so that gradient of the brightness level near a boundary of the indentation becomes maximum. A binarization part 13 automatically estimates a threshold level to distinguish the indentation from the background in a digital image signal 12 adjusted in the focusing control part 11 and binarizes the digital image signal 12 to output a binary image signal 14. An indentation vertex detecting part 15 has a function to detect the indentation apex from an intersection point of two approximate lines of two sides of the indentation in a binary image formed by the binary image signal 14 and, a function to directly detect the indentation apex by scanning the binary image from near the center of the indentation. An indentation vertex selection part 16 selects one of two kinds of apexes detected by two functions of the indentation vertex detecting part 15, regarding each apex of the indentation, according to a predetermined rule. An indentation size measuring part 17 calculates the length of two diagonal lines of a quadrilateral formed by connecting four vertices selected in the indentation vertex selection part 16. A sample stage 19 can be moved up and down by the autofocusing part 10, and can be moved horizontally.

Figure 5:
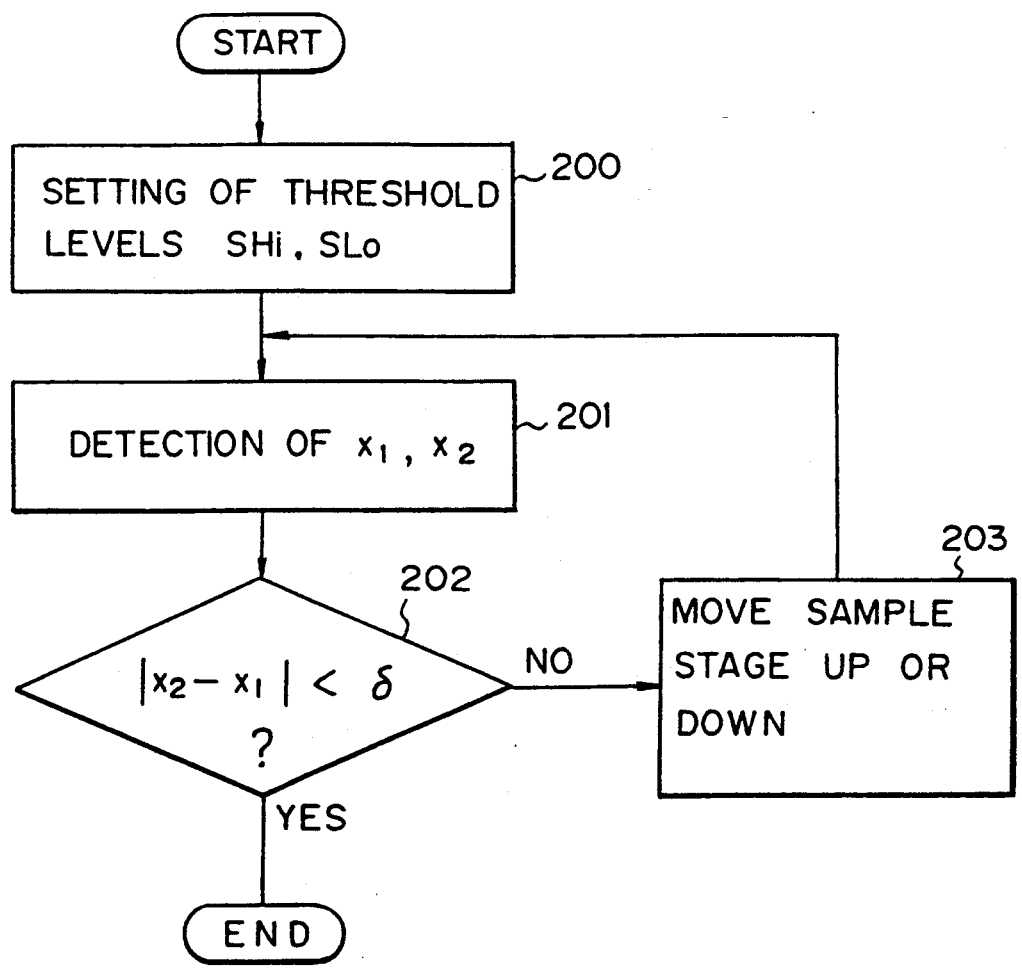
FIG. 5 is a flow chart representing a process in a focusing control part 11 shown in FIG. 4.

An operation of the focusing control part 11 is described referring to FIGS. 5 to 7.

Figure 6A:
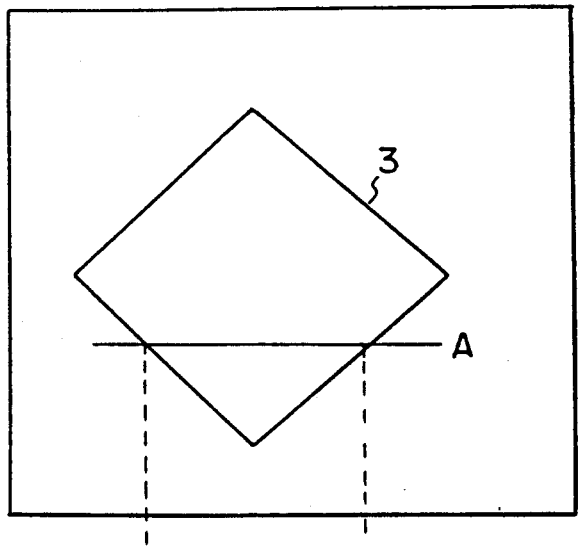
FIGS. 6A to 6C and FIGS. 7A to 7C are diagrams for explaining the process in the focusing control part 11.
Figure 6B:
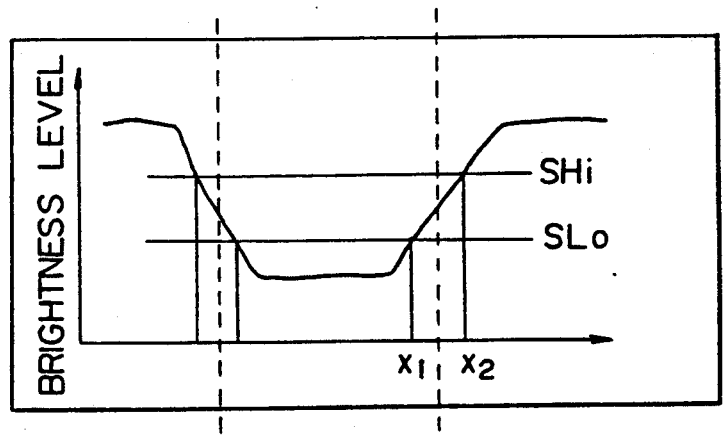
Figure 6C:
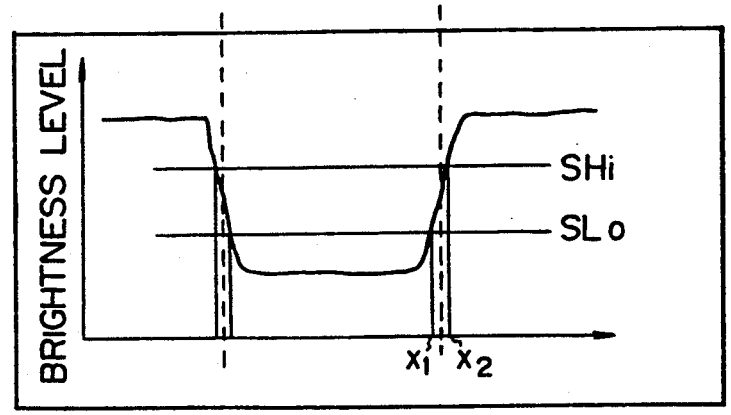
Figure 7A:
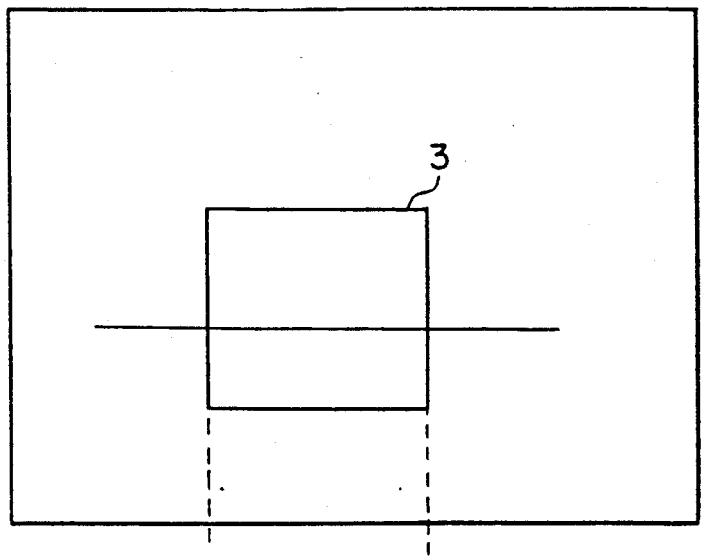
Figure 7B:
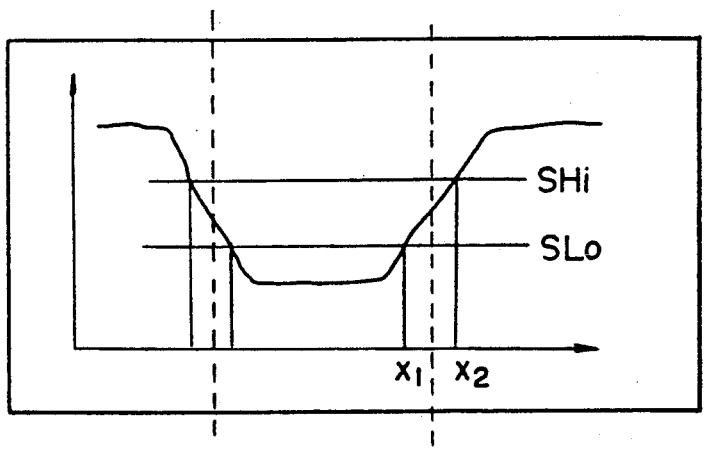
Figure 7C:
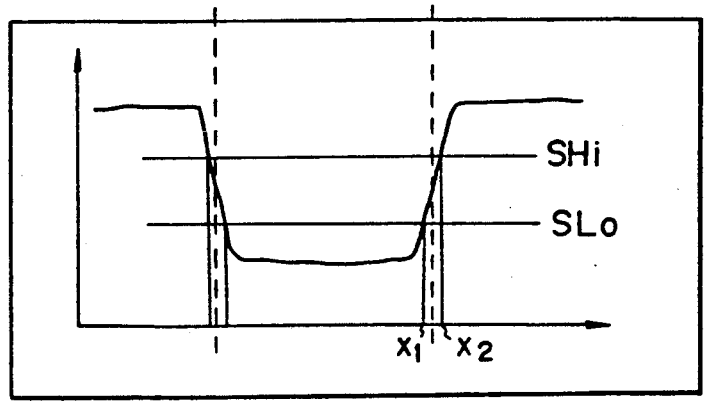

FIG. 5 is a flow chart representing operation of the focusing control part 11. FIG. 6A represents an image of the indentation 3 in the case where the image of the indentation 3 is picked-up so that sides of the indentation are at an angle of about 45° to the screen. FIGS. 6B and 6C show brightness levels of pixels on line A (FIG. 6A), before and after focusing, respectively. FIGS. 7A to 7C are similar to FIGS. 6A to 6C and show the case where the image of the indentation is picked-up by a 45° rotated camera 6. In this case, the image information 7 obtained in the camera 6 can be more effectively used than in the former case. Referring to FIG. 5, threshold levels SHi and SLo are predetermined as to higher level and lower level, respectively (step 200). Positions $x_1$, $x_2$ where pixels have the levels SLo and SHi, respectively, are detected (step 201). If an absolute value of a difference between $x_1$ and $x_2$ is not smaller than a predetermined value $\delta$ (step 202), the sample stage 19 is moved up or down by the autofocusing part 10 (step 203) and then step 201 is again executed.

An operation of the binarization part 13 is described referring to FIGS. 8 to 12.

Figure 8:
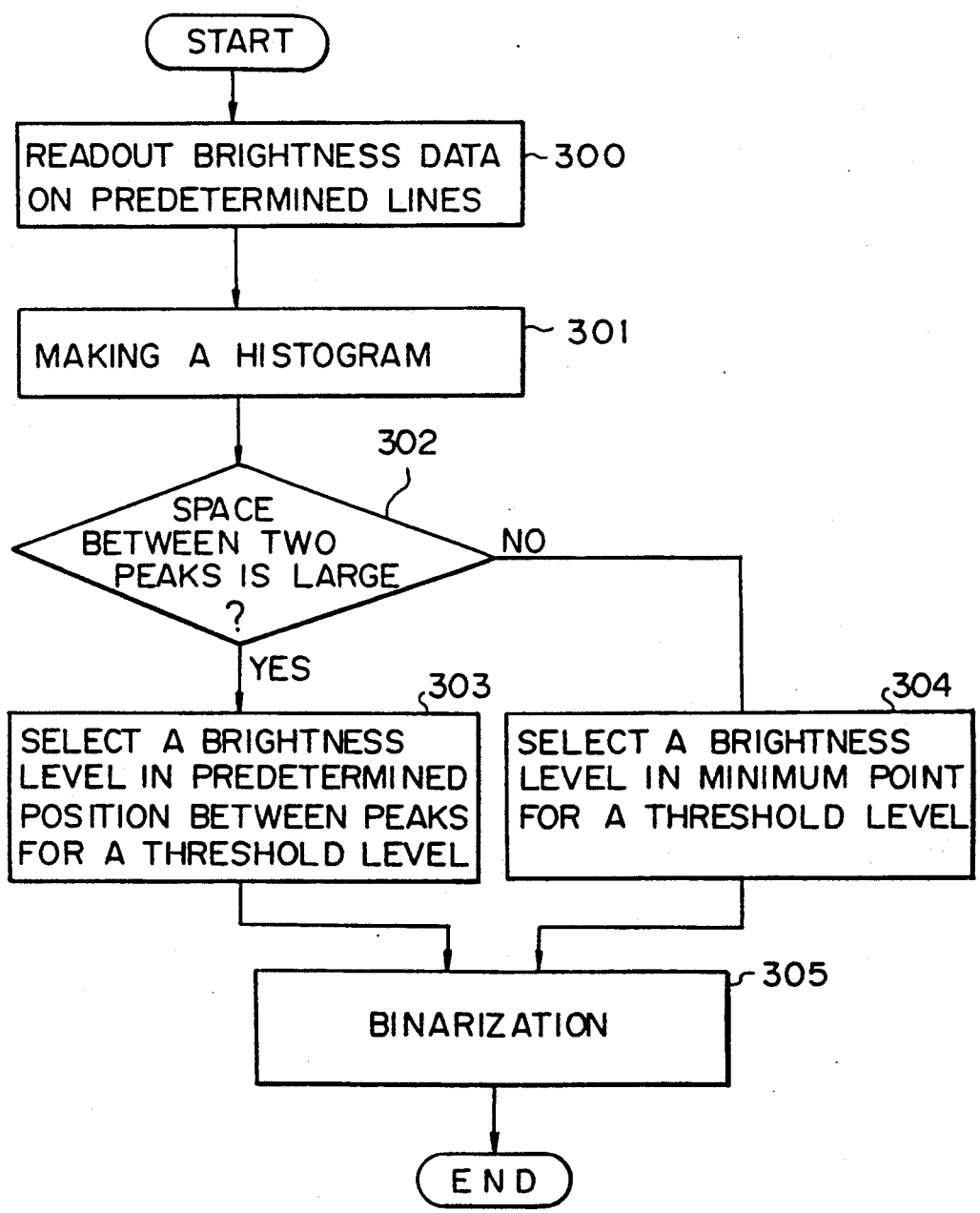
FIG. 8 is a flow chart representing a process in a binarization part 13 shown in FIG. 4.
Figure 9:
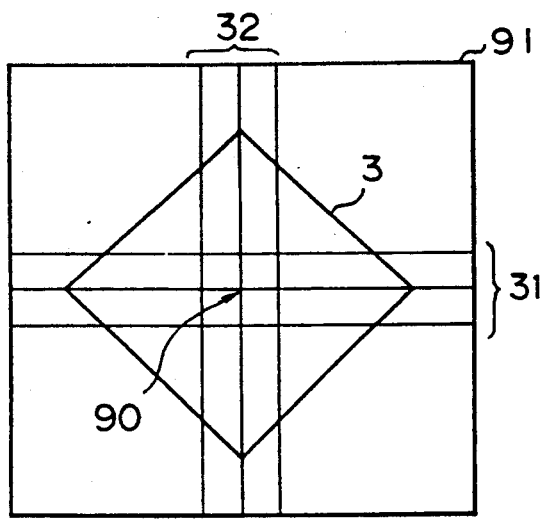
FIGS. 9, 10, 11A and 11B, and 12A to 12C are diagrams for explaining the process in the binarization part 13.
Figure 10:
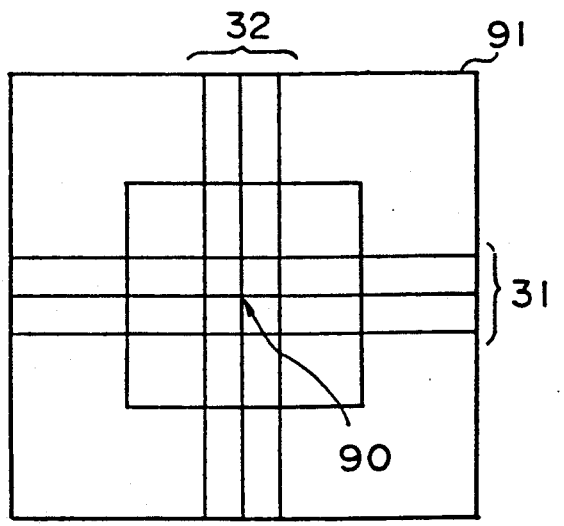

FIG. 8 is a flow chart representing the operation of the binarization part 13. The testing machine 4 memorizes an indented place and brings the microscope 5 to that place for measurement. Therefore, as shown in FIG. 9 or FIG. 10, the image of the indentation 3 is roughly placed at the center 90 of a visual field 91 of the camera 6.

Accordingly, data including values for both indentation and background can be obtained by reading out brightness level data on a plurality of (in this case: 3) horizontal or vertical lines 31 or 32 lying near the center 90 of the visual field 91 (step 300).

A frequency distribution (referred to hereinafter as a histogram) of the brightness levels is made from the readout data (step 301). A histogram made by grouping several successive brightness levels is adequate, rather than making a histogram for all brightness levels. FIG. 11 shows examples of the histogram made by grouping five successive levels.

Figure 11A:
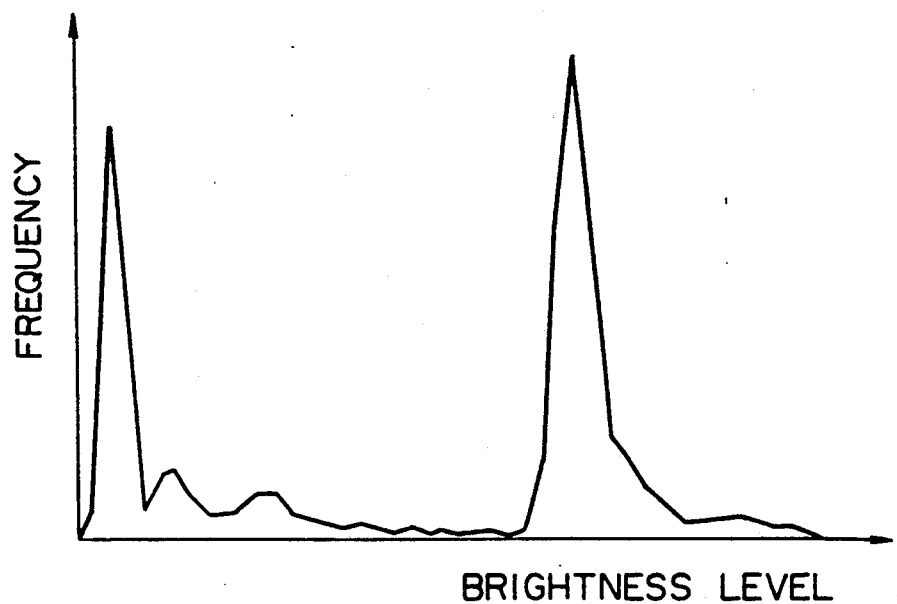
Figure 11B:
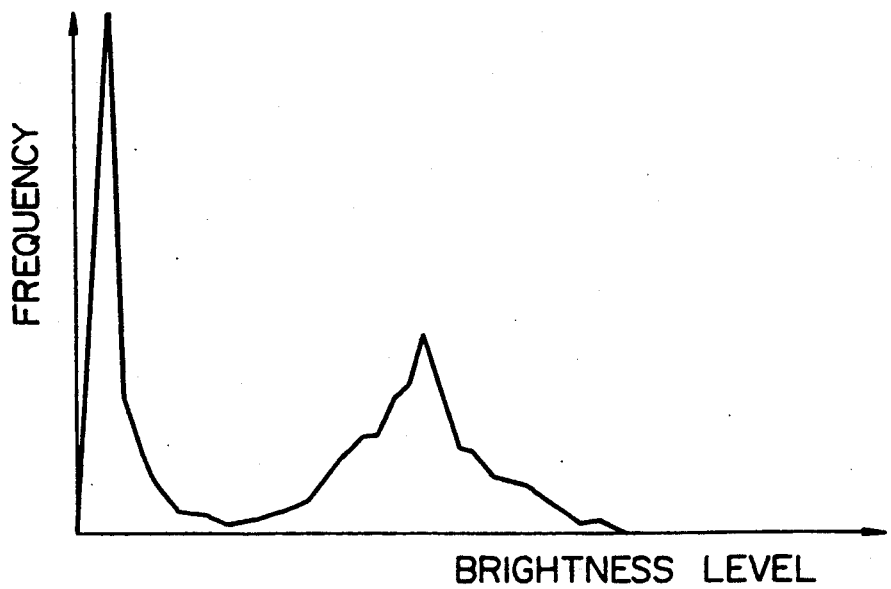
Figure 12A:
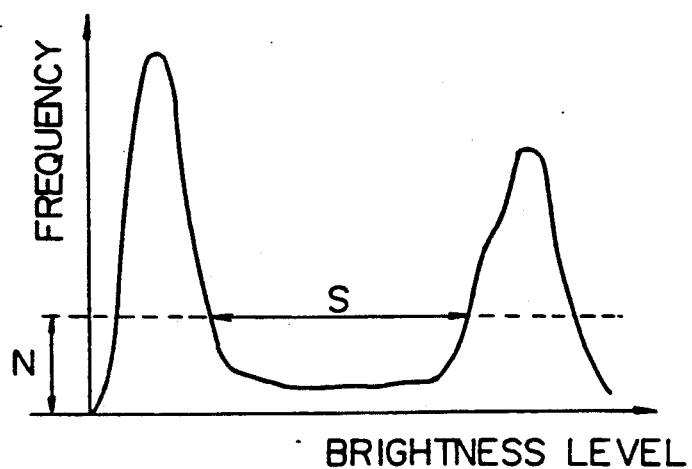
Figure 12B:
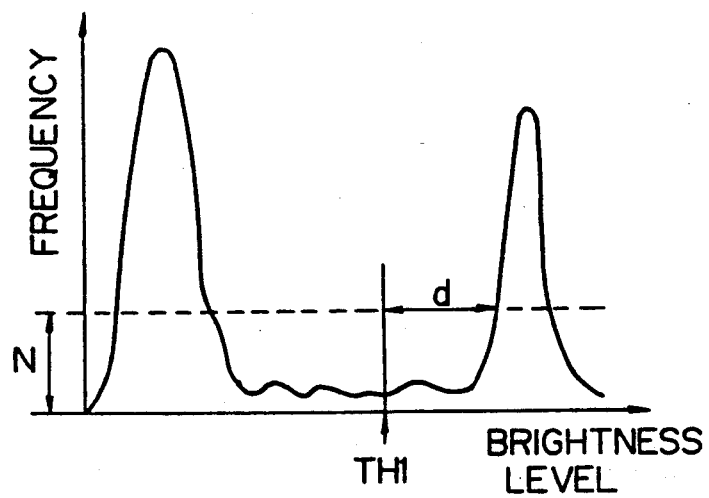
Figure 12C:
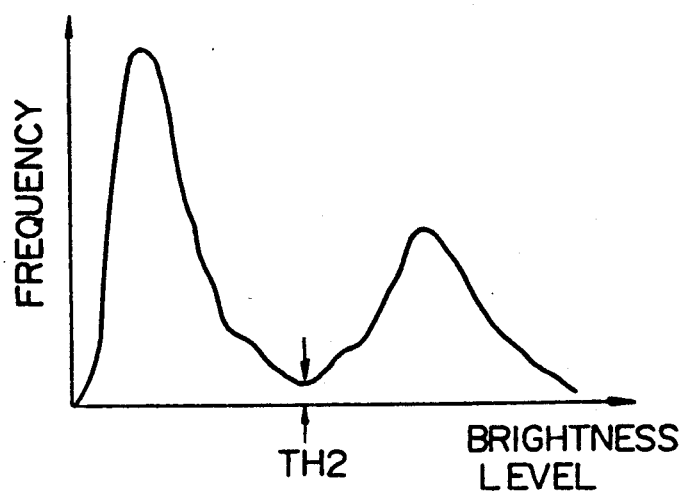

FIG. 11A shows an example wherein a surface of the sample is specular and FIG. 11B shows another example wherein a surface of the sample is a matrix organized surface. The left side peak corresponds to the indentation and the right side peak corresponds to the background. Generally, the right side peak (background) is positioned toward white level and sharpened in the case of a specular sample, and the right side peak is broadened in the case of a matrix organized surface because of its surface pattern. Therefore, as shown in FIG. 12A, space S between two peaks is calculated based on a predetermined threshold frequency N and whether the space S is larger than a predetermined level difference C, or not, is then decided (step 302). If the space S is larger than the value C, as shown in FIG. 12B, a threshold level for binarization is settled at a position between the peaks based on an empirically predetermined constant d (step 303). Constant d defines the position of the brightness threshold level which in FIG. 12B is constant d from where a peak crosses the threshold frequency N. If the space S is smaller than the value C, the threshold level for binarization is settled at a minimum point between the peaks (step 304). Then using this threshold level, the digital image signal is binarized to make a binary image (step 305). Adequate values of the aforementioned constants N, S, C, and d are determined for each hardness tester because the values must be altered if brightness of a light source or sensitivity of the camera is different.

Next, an operation of the indentation apex detecting part 15 is described referring to FIG. 13 to FIG. 23.

Figure 13:
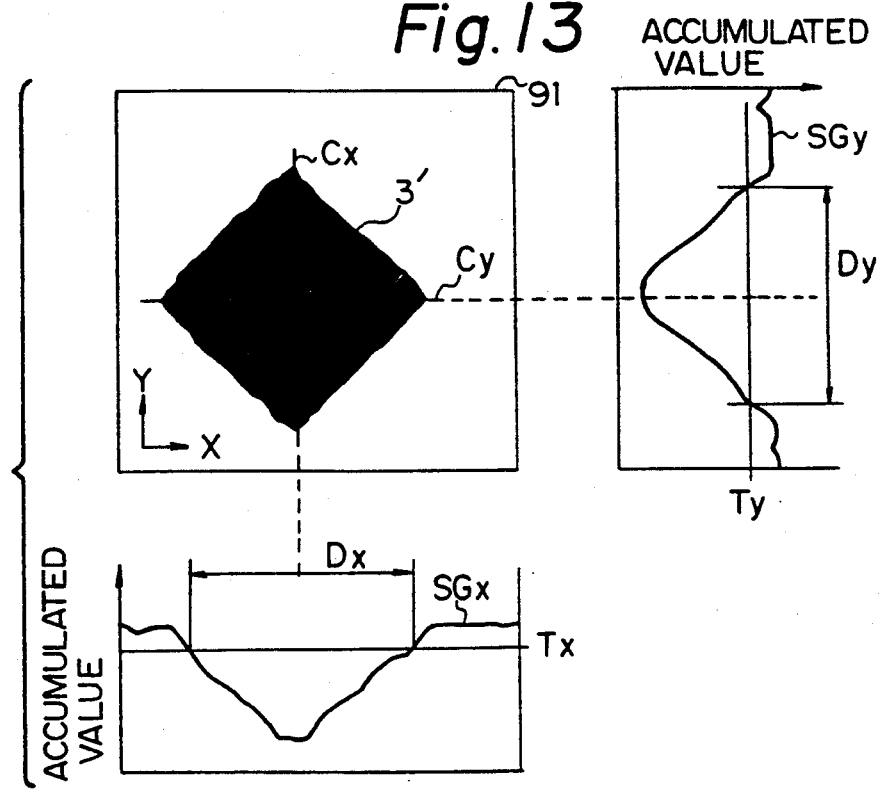
FIGS. 13, 14A, 14B, 15A, 15B, 16, 17A to 17D, 18, 19A, 19B, 20A, 20B, 21, and 22A to 22D are diagrams for explaining processes in an indentation vertex detecting part 15 shown in FIG. 4.

FIG. 13 shows a binary image 3' of an indenter 3, a curved line $SG_x$ obtained by plotting accumulated values of binary pixels on lines parallel to a Y axis, and a curved line $SG_y$ obtained by plotting accumulated values of binary pixels on lines parallel to an X axis. Extents of the indentations $D_x$ and $D_y$ can be determined by $SG_x$ and $SG_y$ using predetermined threshold levels $T_x$ and $T_y$. It can be considered that a straight line $C_x$ which passes through a middle point of the extent $D_x$ and which is parallel to the Y axis equally divides the indentation, and that a straight line $C_y$ which passes through a middle point of the extent $D_y$ and which is parallel to the X axis also equally divides the indentation.

Figure 14A:
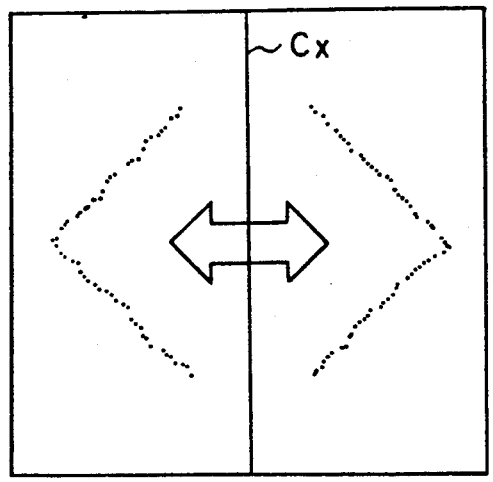
Figure 14B:
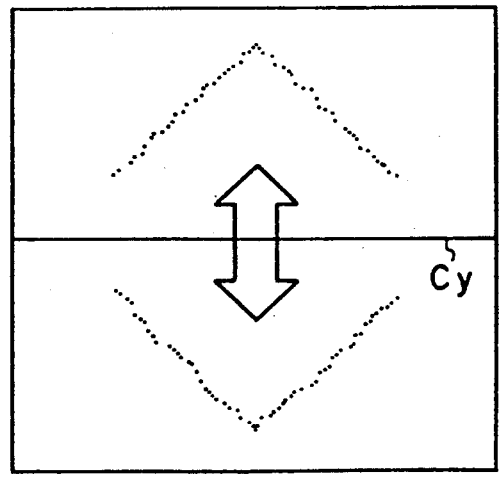
Figure 15A:
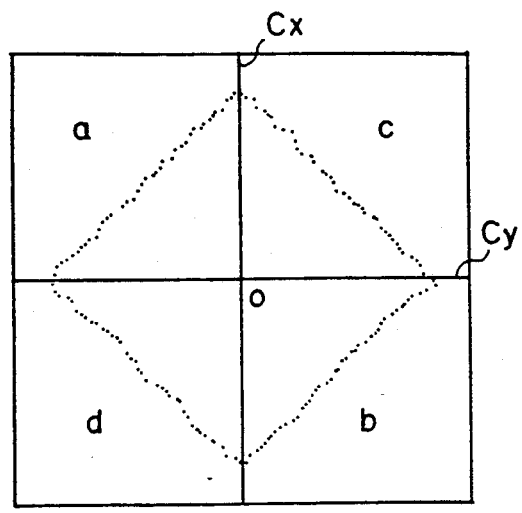
Figure 15B:
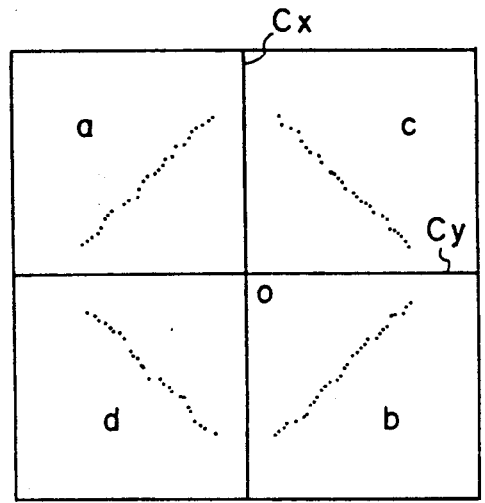
Figure 16:
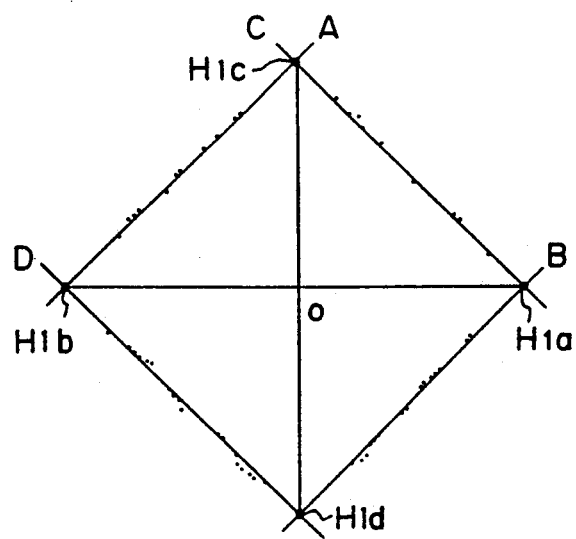

Thus, as shown in FIG. 14A, pixels corresponding to boundary of the indentation are found by scanning the binary image data from pixels on the line $C_x$ toward left and right, and by selecting first pixels having a value of "1" or pixels one pixel before those pixels. Also, as shown in FIG. 14B, pixels corresponding to the boundary of the indentation are found by scanning the binary image data from pixels on the line $C_y$ upward and downward, and by selecting first pixels having a value of "1" or pixels one pixel before those pixels. As shown in FIG. 15A, pixels corresponding to the boundary of the indentation are obtained in those processes. As shown in FIG. 15B, these pixels are divided into four pixel groups by straight lines $C_x$ and $C_y$, and pixels near the lines $C_x$ and $C_y$ are excluded. Applying the least square method to each pixel group, four lines (for example, straight lines) A, B, C, D which approximate sides of the indentation are obtained as shown in FIG. 16. Coordinates of intersection points $H_{1a}$, $H_{1b}$, $H_{1c}$, and $H_{1d}$ are calculated from formulae representing the lines A, B, C, and D. The intersection points $H_{1a}$, $H_{1b}$, $H_{1c}$, and $H_{1d}$ correspond to vertices of the indentation. An intersection point O of a line connecting $H_{1a}$ and $H_{1b}$ and a line connecting $H_{1c}$ and $H_{1d}$ corresponds to the center of the indentation.

Figure 17A:
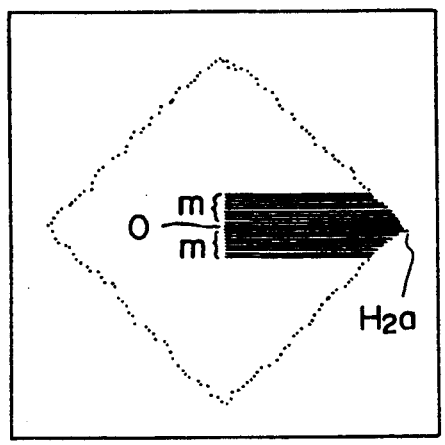

Next, as shown in FIG. 17A, the binary image data are scanned from a starting point O toward an X direction to find a first pixel having a value of "1" or a pixel one pixel before that pixel as a vertex, and the length (number of pixels) of a line segment from the starting point to the vertices are calculated. Similar operations are performed m times successively changing the Y coordinate toward a positive direction and negative direction. The longest line segment is selected from among 2m+1 line segments, and another apex of the indentation $H_{2a}$ is determined at the vertex of the longest line segment.

Figure 17B:
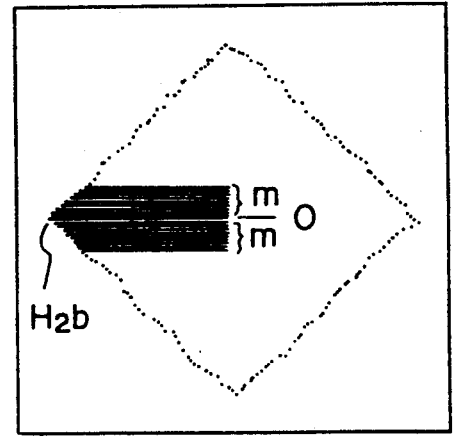
Figure 17C:
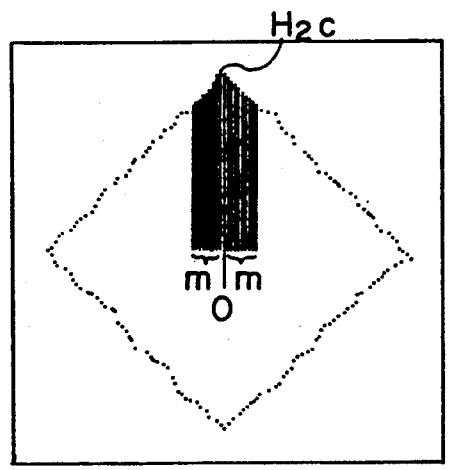
Figure 17D:
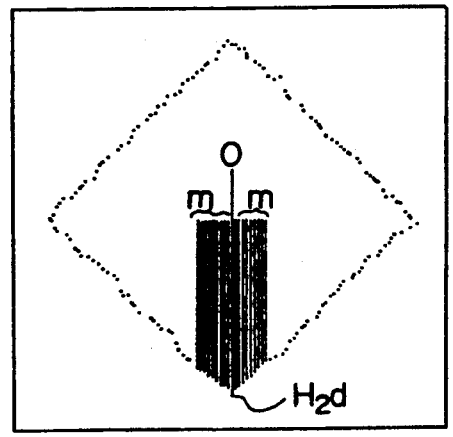
Figure 18:
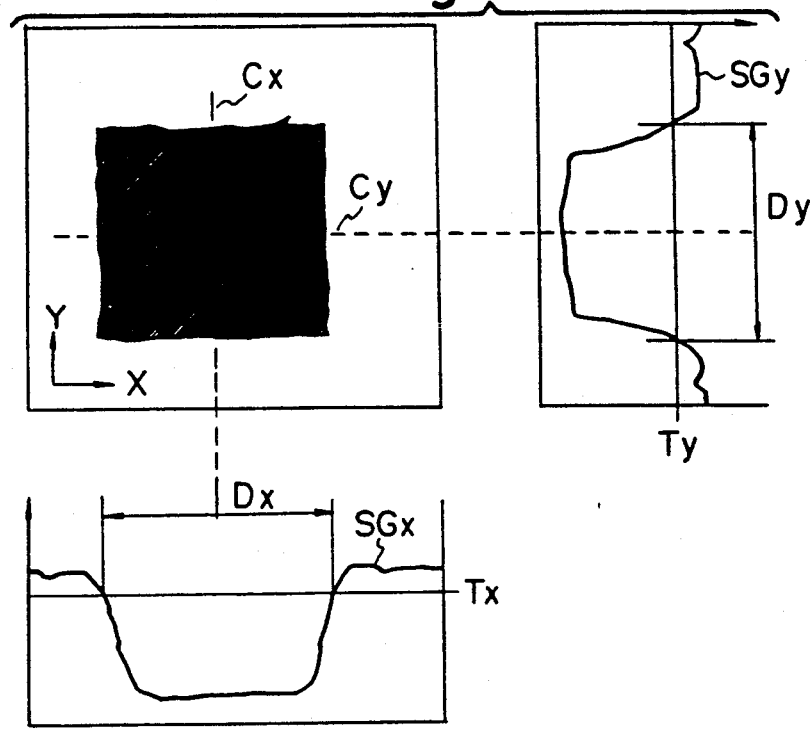
Figures 19A, 19B:
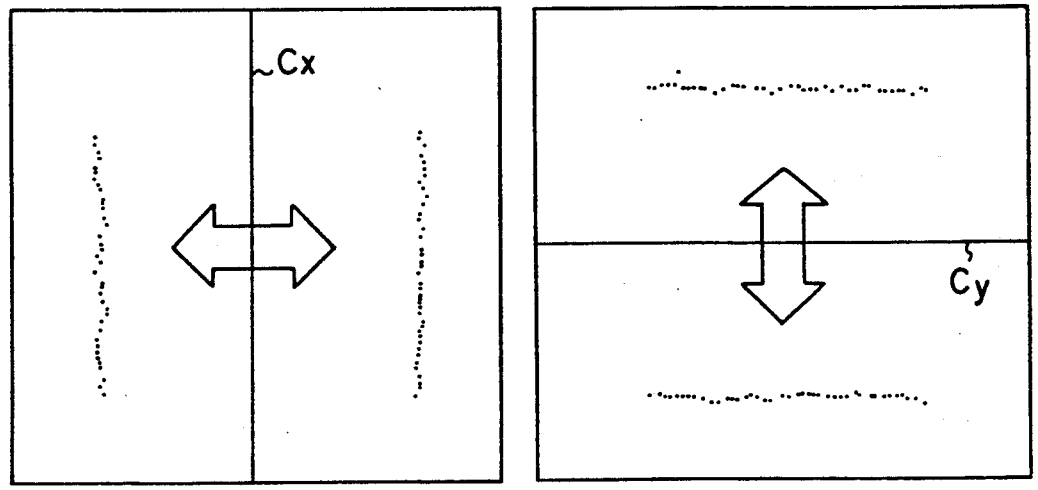
Figure 20A:
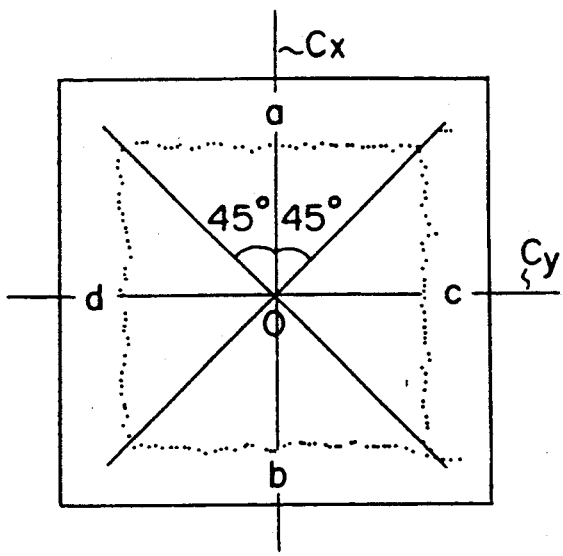
Figure 20B:
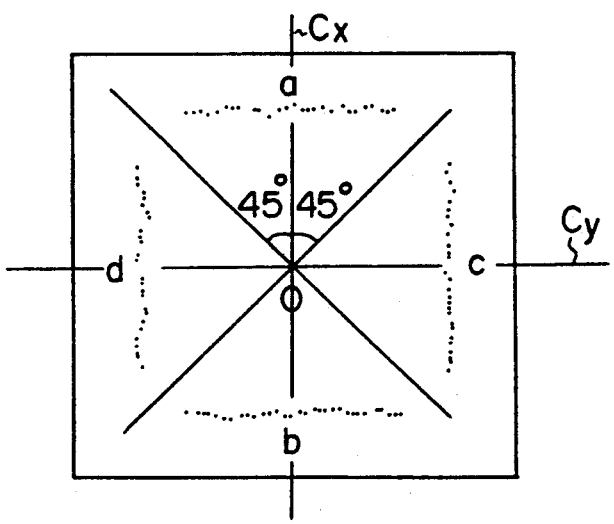
Figure 21:
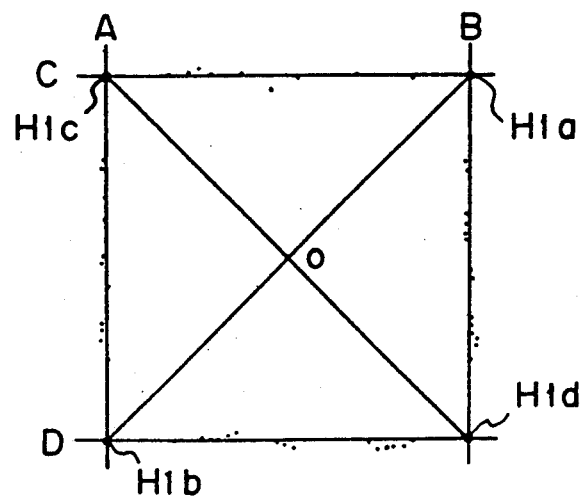
Figure 22A:
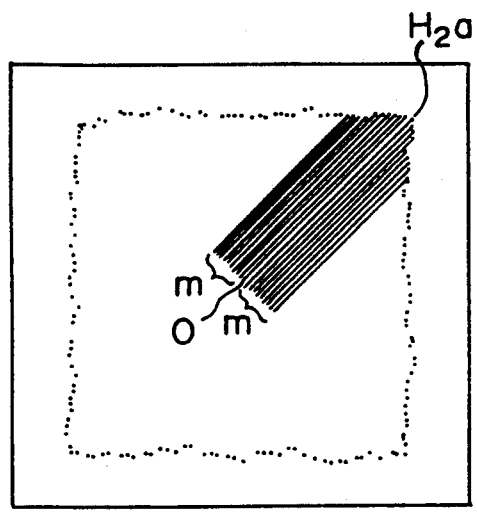
Figure 22B:
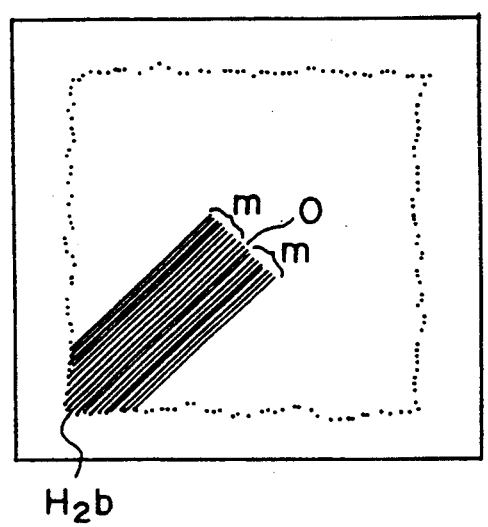
Figure 22C:
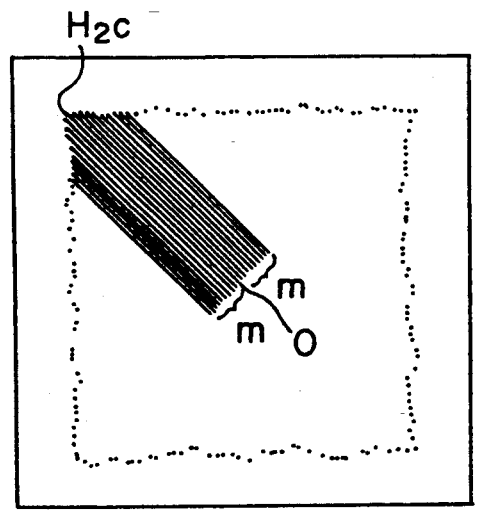
Figure 22D:
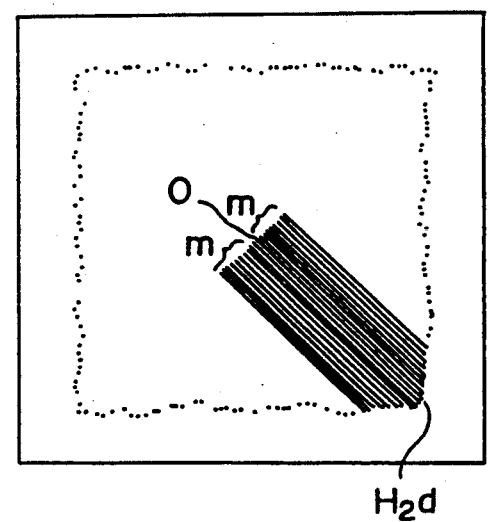

Apexes $H_{2b}$, $H_{2c}$ and $_{2d}$ can be determined as shown in FIGS. 17B to 17D by a similar process.

The number m is predetermined considering testing conditions such as kind of sample, indenting load, and conditions of the optical system. The aforementioned intersection point of $C_x$ and $C_y$ can be also used as the reference point O. Thus, two kinds of indentation apexes $H_{1a}$ to $H_{1d}$ and $H_{2a}$ to $H_{2d}$ are determined. In the case where the image is picked-up by a 45° rotated camera, the indentation edge points $H_{1a}$ to $H_{1d}$ and $H_{2a}$ to $H_{2d}$ can be obtained by a similar process as shown in FIGS. 18 to 22 which are diagrams similar to those of FIGS. 13 to 17.

Figure 23A:
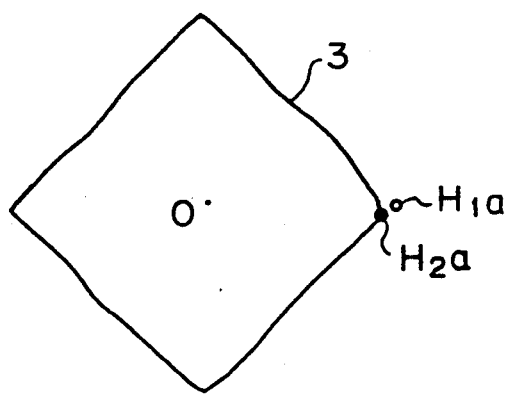
FIGS. 23A and 23B are diagrams for explaining a process in an indentation vertex selection part 16 shown in FIG. 4.
Figure 23B:
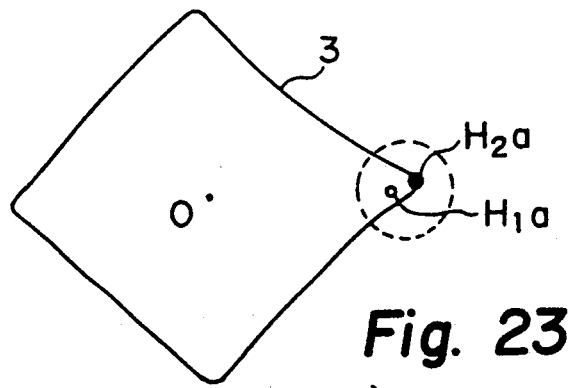
Figure 23C:
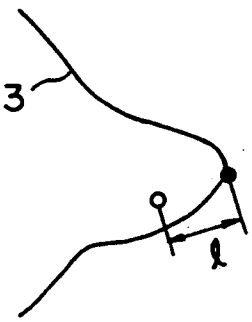

An operation of the indentation apex selection part 16 is described referring to FIG. 23. Selection in the indentation vertex selection part 16 is performed according to the following rules:

(1) If a mean deviation in the aforementioned determination of the approximate lines A, B, C, and D (FIG. 16) using the least square method is larger than a predetermined value, then $H_2$ is employed.

(2) If the distance between O and $H_1$ is larger than the distance between O and $H_2$, then $H_2$ is employed (FIG. 23A).

(3) In the case where the distance between O and $H_1$ is smaller than the distance between O and $H_2$, if the distance l between $H_1$ and $H_2$ is larger than a predetermined value (l>l'), $H_1$ is employed, and if smaller (l<l'), $H_2$ is employed (FIG. 23B).

Indentation apexes ($H_a$, $H_b$, $H_c$, $H_d$) obtained by selecting each vertex from two kinds of apexes ($H_{1a}$, $H_{1b}$, $H_{1c}$, $H_{1d}$) and $H_{2a}$, $H_{2b}$, $H_{2c}$, $H_{2c}$, $H_{2d}$) are very close to those obtained by human decision through visual observation.

The indentation size measuring part 17 measures length of diagonals $l_1$, $l_2$ of quadrilateral $H_a$-$H_b$-$H_c$-$H_d$ based on coordinates of $H_a$, $H_b$, $H_c$, $H_d$ determined in the indentation vertex selection part 16.

The hardness number calculation part 18 calculates, for example, Vickers hardness number $H_v$ from indenting load P and mean value l of the length $l_1$ and $l_2$, in accordance with the following equation:

$$H_v = 2P \sin 68°/l^2 = 1.854\, P/l^2 [\text{kg/mm}^2]$$

In the aforementioned equation, an estimate of the length l is used as a surface area of the indentation, because an actual surface area can not be easily obtained.

Figure 24:
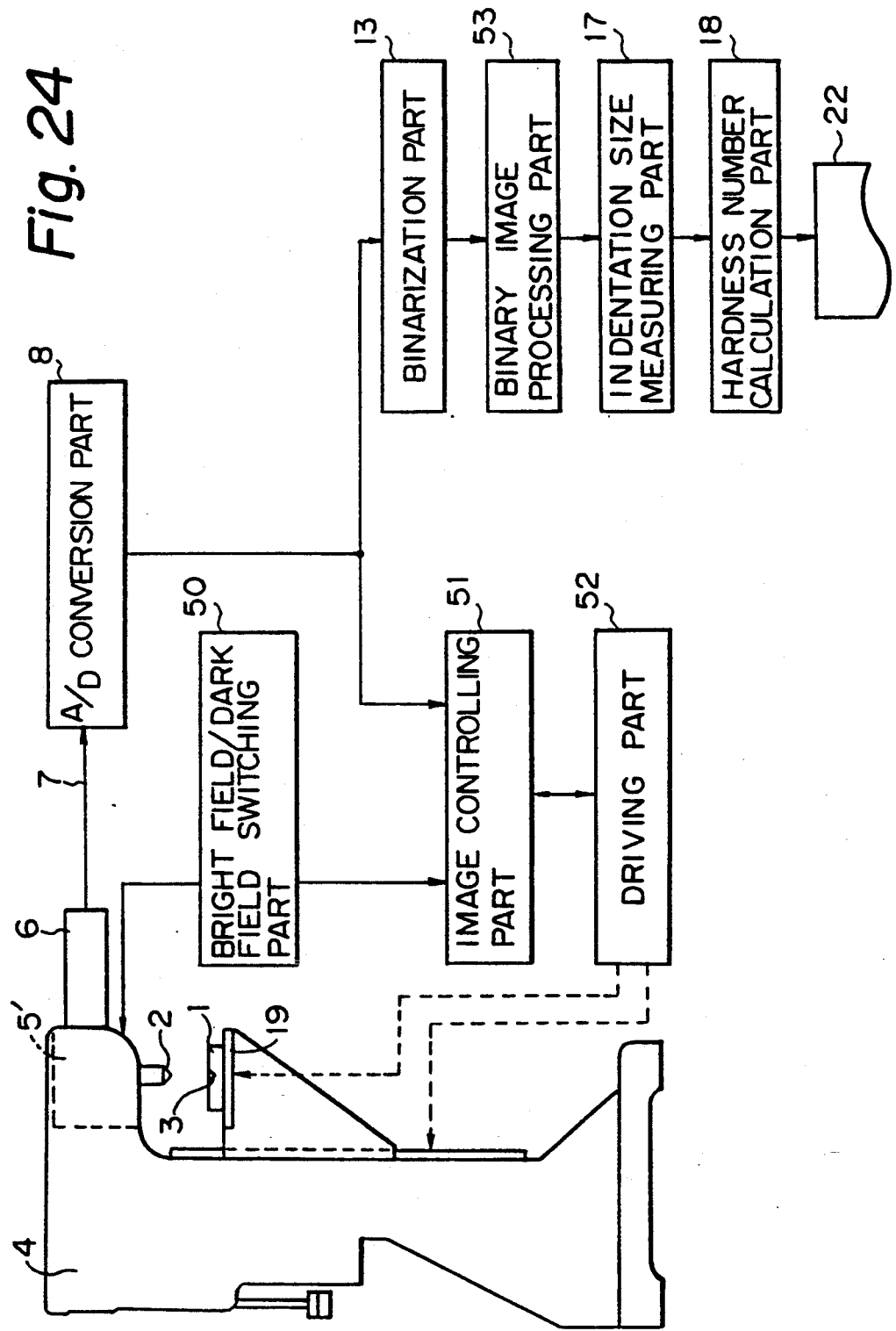
FIG. 24 is a diagram representing a second embodiment of the indentation hardness tester according to the present invention.
Figure 25:
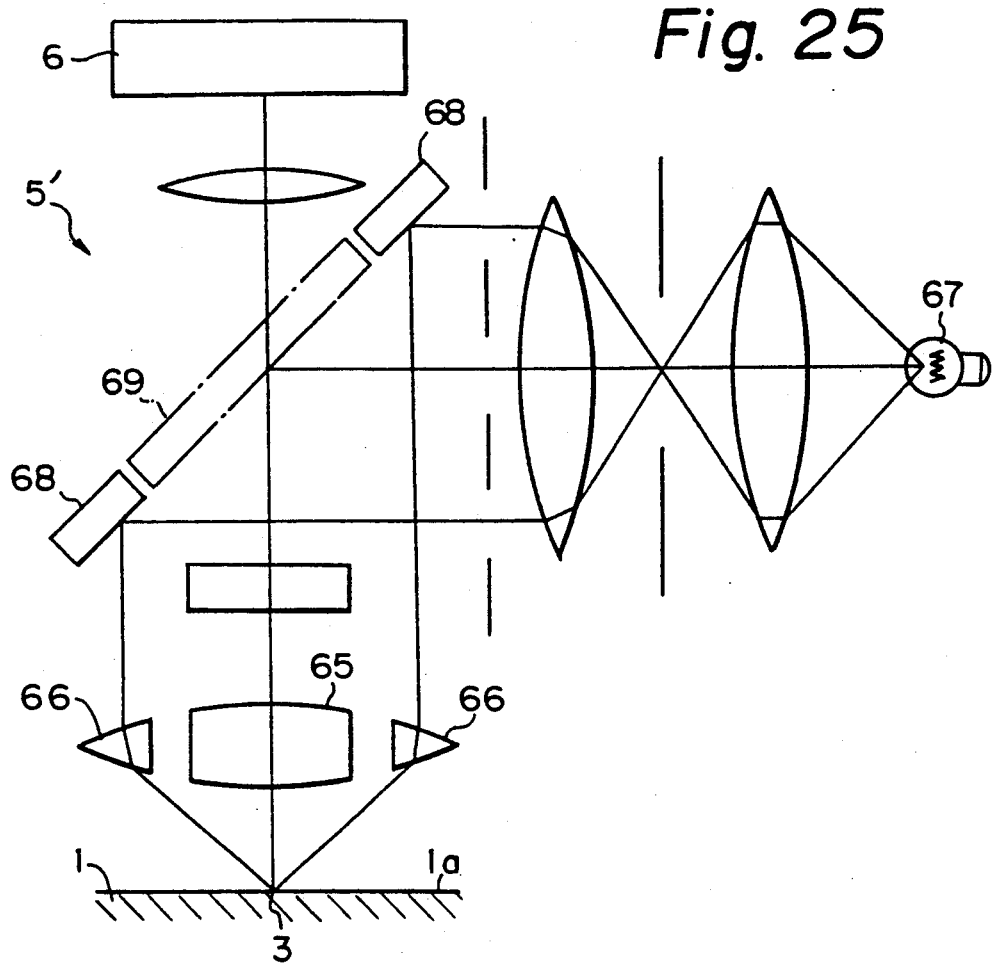
FIG. 25 is a diagram representing a detailed construction of a microscope 5' shown in FIG. 24.

FIG. 24 shows a second embodiment of the present invention. The same reference numerals as used in FIG. 4, and thus a description thereof is left out. FIG. 25 shows a detailed construction of a microscope 5'.

The microscope 5' comprises an objective lens 65 and a ring-shaped lighting lens 66 surrounding the objective lens 65.

Rays of light from a light source 67 are reflected by a ring-shaped mirror 68 to be introduced into the lighting lens 66, and are refracted in the lighting lens 66 to illuminate a surface of a testing piece 1 obliquely at a predetermined angle.

Figure 26A:
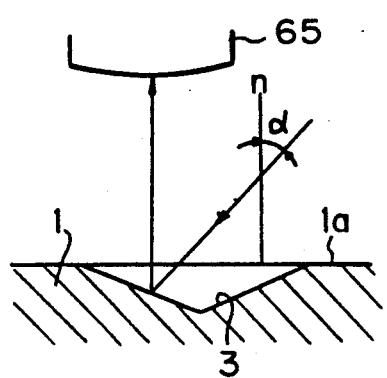
FIGS. 26A and 26B are diagrams explaining a dark field type image of an indentation.
Figure 26B:
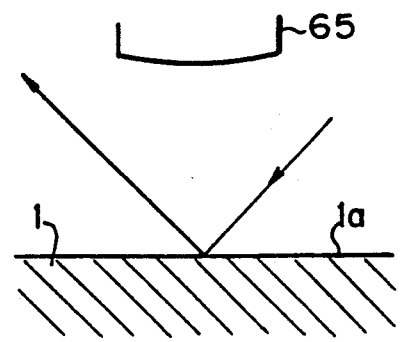

In the case of measuring the Vickers hardness number using an indenter having a face angle of 136°, as shown in FIG. 26A, the illumination angle α with a normal line n of the surface 1a of the testing piece 1 is ideally 44°, and may be 44°±8° to perform actual measurement. If the illumination angle α falls into that range, rays of light incident upon the inclined surface of the indentation are reflected in the direction of the normal line n and enter the objective lens 65 of the microscope 5', and rays of light reflected by any other area scarcely enter the objective lens 65, as shown in FIG. 26B. A more preferable range of the illumination angle α is 44°±6°.

A bright field type image can be obtained in this example of the microscope. To perform this object, a half mirror 69 is provided inside the microscope 5'. The half mirror 69 is arranged so as to be displaced between an operative position on the main optical axis of the microscope 5' and a non-operative position far away from the main optical axis through drive means (not shown), by a bright field/dark field switching part 50 shown in FIG. 24. Additionally, while the half mirror 69 is positioned at the operative position represented by a dashed line in FIG. 25, the aforementioned optical path going through the ring-shaped mirror 68 is intercepted by a blocking-off means (not shown), and only rays of light reflected by the half mirror 69 pass through the objective lens 65 and illuminate surface 1a of the testing piece 1 in the direction of the normal line n. Only rays of light vertically reflected by the surface 1a enter the objective lens 65 of the microscope 5'.

In this example, an alignment process and focusing process of an image are carried out using a bright field type image. Initially, the bright field/dark field switching part 50 is switched to the bright field side. Then, a bright field type image as shown in FIG. 2A or FIG. 3A is obtained. An image controlling part 51 performs an image alignment operation and an image focusing operation utilizing this bright field type digital image signal.

Figure 27:
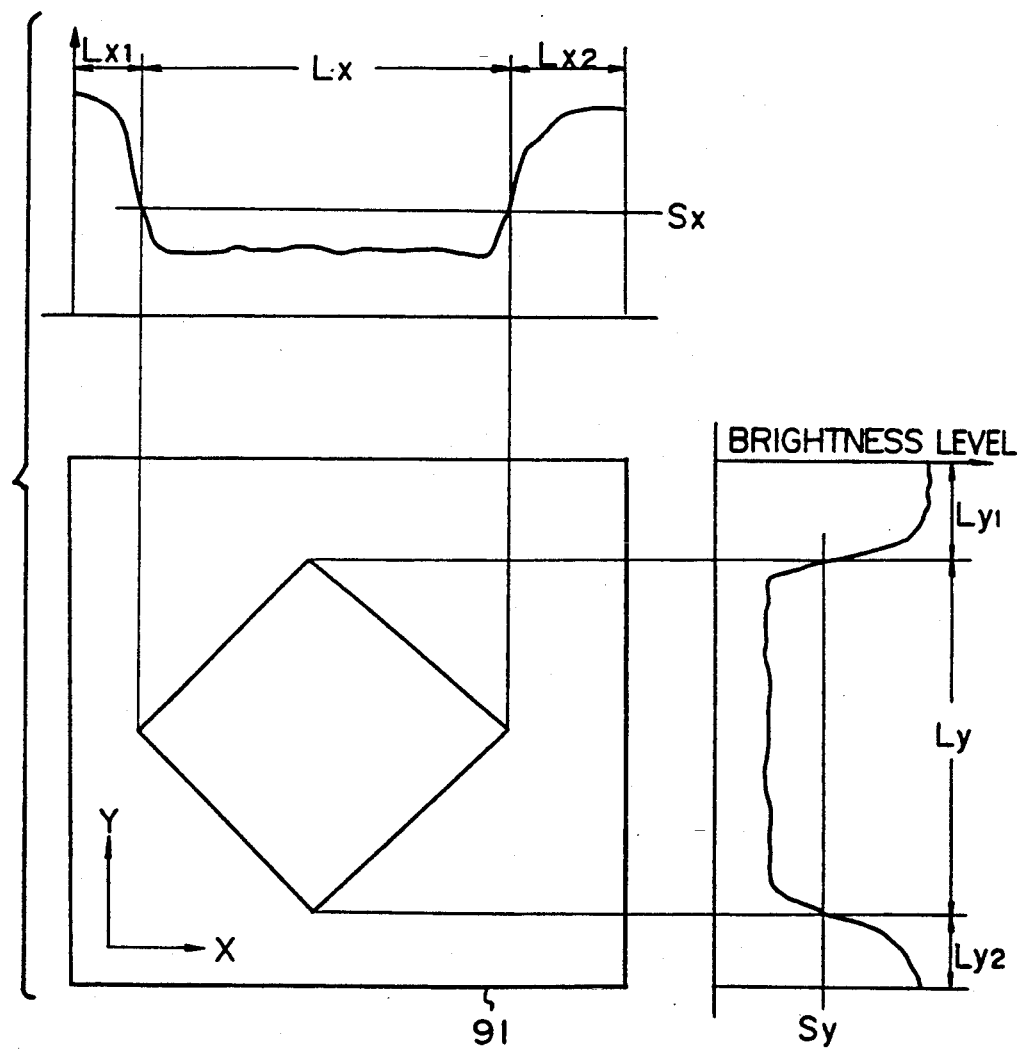
FIG. 27 is a diagram for explaining an image alignment operation in an image controlling part 51 shown in FIG. 24.

The image alignment operation in the image controlling part 51 is described referring to FIG. 27.

The image alignment operation is carried out in order to place the image of the indentation at the center of visual field 91 of the camera 6 so that the dark field type image is clearly obtained. The sample stage 19 is arranged so as to be moved in an X-y plane perpendicular to the main optical axis of the microscope 5'.

As shown in FIG. 27, threshold levels $S_x$, $S_y$ are settled in X, Y directions, respectively. Brightness levels of pixels on two center lines which are parallel to the X, Y directions, respectively, are scanned to determine length $L_x$, $L_y$ of intervals of pixels having a lower brightness level than $S_x$, $S_y$, respectively, and a length $L_{x1}$, $L_{x2}$, $L_{y1}$, $L_{y2}$ of portions on both sides of the intervals, as shown in FIG. 27. If $L_{x1}-L_{x2}>\Delta L_x$, the sample stage 19 is moved to the $L_{x1}$ side, and if $L_{x2}-L_{x1}>\Delta L_x$, the sample stage is moved to the $L_{x2}$ side, wherein $\Delta L_x$ is predetermined as a permitted deviation. A similar operation is also carried out in a Y direction. The image alignment operation is completed when the following condition is satisfied:

$$|L_{x1}-L_{x2}|<\Delta L_x$$

$$|L_{y1}-L_{y2}|<\Delta L_y$$

The image focusing operation in the image controlling part 51 is similar to the operation of the focusing control part 11 described referring to FIG. 5 to FIG. 7, and thus the description thereof is left out.

After the image alignment operation and the image focusing operation are finished, the bright field/dark field switching part 50 is switched to the dark field side.

The dark field type image is picked up by the camera, converted in A/D conversion part 8, and binarized in binarization part 13. An operation of the binary image processing part 53 is similar to the operations of the indentation apex detecting part 15 and the indentation apex selection part 16.

A more clear image of an indentation is obtained in the dark field image than the bright field image as explained before. Therefore, image processing in the binarization part 13 or the binary image processing part 53 can be simplified. For example, a predetermined value can be used for the threshold value to obtain a binary image instead of the value determined from a histogram as explained referring to FIG. 11 to FIG. 12, and coordinates of edge points $H_{1a}$ to $H_{1d}$ determined from intersection point of two approximate lines can be directly used as apexes $H_a$ to $H_d$ for determination of the indentation size.

It should be noted that in FIGS. 4 and 24, an image of the indentation including all vertices thereof, is picked up by camera 6 which has a two-dimensional image sensor having a visual field larger than the image of the indentation.

We claim:

1. An indentation hardness tester for determining the hardness number of a testing piece even when the indentation formed in the testing piece is incorrectly aligned and/or shaped, said indentation hardness tester comprising:

a testing machine for forming an indentation on a testing piece by indenting a surface of the testing piece with a pyramid shape indenter under a predetermined indenting load;

a camera attached to a microscope for picking up a two-dimensional image of said indentation;

conversion means for converting the two-dimensional image into a binary image of said indentation;

an indentation vertex determining means for determining two-dimensional positions of vertices and a center of said indentation regardless of alignment and shape of the indentation formed in the testing piece based on said binary image;

an indentation size measuring means for measuring diagonal lengths of said indentation based on said determined two-dimensional positions of the vertices of said indentation; and a hardness number calculation means for calculating a hardness number base don the diagonal lengths and said predetermined indenting load.

2. An indentation hardness tester comprising:

a testing machine for forming an indentation on a testing piece by indenting a surface of the testing piece with a pyramid shape indenter under a predetermined indenting load;

a camera attached to a microscope for picking up a two-dimensional image of said indentation;

conversion means for converting the two-dimensional image into a binary image of said indentation;

an indentation vertex determining means for determining two-dimensional positions of vertices and a center of said indentation based on said binary image;

an indentation size measuring means for measuring diagonal lengths of said indentation based on said determined two-dimensional positions of the vertices of said indentation;

a hardness number calculation means for calculating a hardness number based on the diagonal lengths and said predetermined indenting load; and wherein said indentation vertex determining means comprises:

an indentation vertex detecting means for detecting a set of first coordinates of the vertices of said indentation based on intersection points of lines which approximate sides of said indentation, and detecting a second set of coordinates of the vertices of said indentation based on the longest line segment from among a plurality of line segments extending parallel to each other from near the center of said indentation to the boundary of said indentation in a predetermined set of directions, and an indentation vertex selection part for selecting one set of coordinates from said first and second set of coordinates which best approximates each vertex of said indentation; and outputting said selected set of coordinates as representing said two-dimensional positions of the vertices of said indentation.

3. An indentation hardness tester as claimed in claim 2, wherein said indentation vertex detecting means determines said lines which approximate sides of said indentation by applying a least squares method to four groups of pixels which correspond to a boundary of said indentation.

4. An indentation hardness tester as claimed in claim 3, wherein said indentation vertex selection means selects said first set of coordinates when a mean deviation of said approximate lines is smaller than a predetermined value, the distance between the center of said indentation and said first set of coordinates is smaller than the distance between the center of said indentation and said second set of coordinates, and the distance between said first and second set of coordinates is larger than a predetermined value; otherwise said second set of coordinates is selected.

5. An indentation hardness tester as claimed in claim 4, further comprising a focusing control means for automatically controlling focus of said image of said indentation.

6. An indentation hardness tester comprising:
a testing machine for forming an indentation on a testing piece by indenting a surface of the testing piece with a pyramid shape indenter under a predetermined indenting load;
a camera attached to a microscope for picking up a two-dimensional image of said indentation;
conversion means for converting the two-dimensional image into a binary image of said indentation;
an indentation vertex determining means for determining two-dimensional positions of vertices and a center of said indentation based on said binary image;
an indentation size measuring means for measuring diagonal lengths of said indentation based on said determined two-dimensional positions of the vertices of said indentation;
a hardness number calculation means for calculating a hardness number based on the diagonal lengths and said predetermined indenting load;
bright field/dark field switching means for controlling said microscope to obtain a bright field type image and a dark field type image;
an image controlling means for performing an alignment process and focussing process of an image utilizing said bright field type image; and
said converting means converts said dark field type image into a binary image.

7. An indentation hardness tester as claimed in claim 6, wherein said indentation vertex determining means determines coordinates of the vertices of said indentation from intersection points of lines which approximate sides of said indentation.

8. An indentation hardness tester as claimed in claim 6, wherein said indentation vertex determining means comprises:

an indentation vertex detecting means for detecting a set of first coordinates of the vertices of said indentation from intersection points of lines which approximate sides of said indentation, and detecting a second set of coordinates of the vertices of said indentation based on the longest line segment from among a plurality of line segments extending parallel to each other from near the center of said indentation to the boundary of said indentation in a set of predetermined directions, and
an indentation vertex selection part for selecting one set of coordinates from said first and second set of coordinates which best approximates each vertex of said indentation; and outputting said selected set of coordinates as representing said two-dimensional positions of the vertices of said indentation.

9. An indentation hardness tester comprising:
a testing machine for forming an indentation on a testing piece by indenting a surface of the testing piece with a pyramid shape indenter under a predetermined indenting load;
a camera attached to a microscope for picking up a two-dimensional image of said indentation, a visual field of said camera being larger than said image of said indentation;
conversion means for converting the two-dimensional image into a binary image of said indentation;
an indentation vertex determining means for determining two-dimensional positions of vertices and a center of said indentation based on said binary image;
an indentation size measuring means for measuring diagonal lengths of said indentation based on said determined two-dimensional positions of the vertices of said indentation; and
a hardness number calculation means for calculating a hardness number based on the diagonal lengths and said predetermined indenting load.

10. An indentation hardness tester comprising:
a testing machine for forming an indentation on a testing piece by indenting a surface of the testing piece with a pyramid shape indenter under a predetermined indenting load;
a camera, having a two-dimensional image sensor, attached to a microscope for picking up a two-dimensional image of said indentation;
conversion means for converting the two-dimensional image into a binary image of said indentation;
an indentation vertex determining means for determining two-dimensional positions of vertices and a center of said indentation based on said binary image;
an indentation size measuring means for measuring diagonal lengths of said indentation based on said determined two-dimensional positions of the vertices of said indentation;
a hardness number calculation means for calculating a hardness number based on the diagonal lengths and said predetermined indenting load.

* * * * *